United States Patent
McCausland et al.

(10) Patent No.: US 12,059,446 B1
(45) Date of Patent: Aug. 13, 2024

(54) COMPOSITIONS AND METHODS FOR SUPPORTING METABOLIC AND ENDOCRINE SYSTEM FUNCTION

(75) Inventors: Calvin W. McCausland, Springville, UT (US); Brent Vaughan, Kearns, UT (US); William J. Hennen, Eagle Mountain, UT (US); David A. Lisonbee, Orem, UT (US)

(73) Assignee: 4Life Patents, LLC, Sandy, UT (US)

( * ) Notice: Subject to any disclaimer, the term of this patent is extended or adjusted under 35 U.S.C. 154(b) by 11 days.

(21) Appl. No.: 11/134,244

(22) Filed: May 20, 2005

(51) Int. Cl.
| | |
|---|---|
| *A61K 36/48* | (2006.01) |
| *A23L 33/105* | (2016.01) |
| *A23L 33/16* | (2016.01) |
| *A23L 33/17* | (2016.01) |
| *A23L 33/19* | (2016.01) |
| *A61K 36/258* | (2006.01) |
| *A61K 36/27* | (2006.01) |
| *A61K 36/42* | (2006.01) |
| *A61K 36/82* | (2006.01) |
| *A61P 3/10* | (2006.01) |

(52) U.S. Cl.
CPC ............ *A61K 36/48* (2013.01); *A23L 33/105* (2016.08); *A23L 33/16* (2016.08); *A23L 33/17* (2016.08); *A23L 33/19* (2016.08); *A61K 36/258* (2013.01); *A61K 36/82* (2013.01); *A61P 3/10* (2018.01); *A23V 2002/00* (2013.01); *A61K 36/27* (2013.01); *A61K 36/42* (2013.01)

(58) Field of Classification Search
CPC . A61K 8/97; A61K 8/98; A61K 8/986; A61K 36/48; A61K 36/258; A61K 36/82; A61K 36/27; A61K 36/42; A23L 33/105; A23L 33/16; A23L 33/17; A23L 33/19; A61P 3/10; A23V 2002/00
See application file for complete search history.

(56) References Cited

U.S. PATENT DOCUMENTS

| | | | | |
|---|---|---|---|---|
| 4,618,494 | A * | 10/1986 | Angers | 424/577 |
| 4,816,563 | A * | 3/1989 | Wilson et al. | 530/344 |
| 5,084,482 | A * | 1/1992 | Hirsch et al. | 514/562 |
| 6,277,396 | B1 * | 8/2001 | Dente | 424/439 |
| 6,468,534 | B1 | 10/2002 | Hennen | |
| 6,866,868 | B1 | 3/2005 | Lisonbee | |
| 6,884,420 | B2 * | 4/2005 | See | 424/195.15 |
| 7,390,512 | B2 * | 6/2008 | Olalde Rangel | 424/728 |
| 2002/0004045 | A1 * | 1/2002 | Pimentel | 424/141.1 |
| 2002/0044942 | A1 * | 4/2002 | Dopson | A61K 39/00 424/184.1 |
| 2002/0119928 | A1 * | 8/2002 | McAnalley | 514/12 |
| 2002/0136785 | A1 * | 9/2002 | Yuan | 424/728 |
| 2004/0091559 | A1 * | 5/2004 | Chatterji | 424/762 |
| 2004/0234513 | A1 * | 11/2004 | See | A61K 31/122 424/94.1 |

FOREIGN PATENT DOCUMENTS

| | | | |
|---|---|---|---|
| EP | 914831 A2 * | 5/1999 | |
| JP | 04149139 A * | 5/1992 | |
| JP | 2002078453 A * | 3/2002 | |
| WO | WO 0103700 A1 * | 1/2001 | |
| WO | WO 2003020026 A1 * | 3/2003 | |
| WO | 2004041071 A2 | 5/2004 | |

OTHER PUBLICATIONS

"Metabolism" Internet Archive Date: Aug. 8, 2002 [Retrieved on Nov. 15, 2007]. Retrieved from the Internet: <URL:http://web.archive.org/web/*/http://users.rcn.com/jkimball.ma.ultranet/BiologyPages/M/Metabolism.html>.*

"Endocrine System" Internet Archive Date: Dec. 2, 2000 [Retrieved on Nov. 15, 2007]. Retrieved from the Internet: <URL:http://web.archive.org/web/*/http://www.biology.clc.uc.edu/courses/bio105/endocrin.htm>.*

Stasiūniene et al. "Peptides Regulating Food Intake and Body Weight". Medicina (Kaunas) vol. 41, No. 12 (2005) 989-1001.*

Ahmed (Diabetes Research and Clinical Practice (2001), vol. 51, pp. 155-161).*

Grover (Mol. and Cell. Biochem. (2002), vol. 241, pp. 53-59).* http://www.easycart.net/BeyondACenturyInc./Herbals_A-B.html—accessed Jan. 2009.*

Chen et al. "Bitter Melon (*Momordica charantia*) Reduces Adiposity, Lowers Serum Insulin and Normalizes Glucose Tolerance in Rats Fed a High Fat Diet". The Journal of Nutrition. vol. 133, No. 4 (2003) 1088-1093.* yeastinfectionadvisor.com. "Lactobacillus GG". Internet Archive Date: Feb. 18, 2007 [Retrieved from the Internet on: May 28, 20140]. Retrieved from the Internet: <URL: http://web.archive.org/web/20070218091349/http://www.yeastinfectionadvisor.com/LactobacillusGG.html>.*

Saxena et al. The Journal of Alternative and Complementary Medicine. vol. 10, No. 2. pp. 369-378 (Year: 2004).*

(Continued)

*Primary Examiner* — Aaron J Kosar
(74) *Attorney, Agent, or Firm* — DENTONS Durham Jones Pinegar

(57) ABSTRACT

A composition for supporting metabolism or the endocrine system of a subject includes transfer factor and one or more support components. The transfer factor is useful for preventing, mitigating the effects of, or reversing autoimmunity, as well as for preventing, mitigating the effects or, or reversing oxidative stress. The one or more support components may prevent misregulation of or facilitate regulation of metabolism or endocrine system of the subject. A support or treatment method includes administering transfer factor to a subject, with or without one or more support components.

13 Claims, No Drawings

(56) References Cited

OTHER PUBLICATIONS

Cicero et al. Acta Diabetol. 41:91-98 (Year: 2004).*

Borkowsky et al., "dialyzable lymphoid extract (DLE) from mice resistant to STZ-induced diabetogenesis can interupt the progress of diabetes in STZ-treated CD-1 mice", Biotherapy, 9(1-3): 149-57 (1996).

Arif et al., "Autoreactive T cell responses show proinflammatory polarization in diabetes but a regulartory phenotype in health", J. Clin. Invest. 113(3):451 63 (2004).

Falorni, "Immunologic and genetic aspects of latent autoimmune diabetes in the adult", Minerva Endocrinol., 28(4):297-312 (2003) (abstract).

Pickup et al., "Inflammation and Activated Innate Immunity in the Pathogenesis of Type 2 Diabetes", Diabetes Care, 27(3):813-23 (2004).

Wen et al., "The Effect of Innate Immunity on Autoimmune Diabetes and the Expression of Toll-Like Receptors on Pancreatic Islets", J. Immunol. 172(5):3173-80 (2004).

\* cited by examiner

COMPOSITIONS AND METHODS FOR SUPPORTING METABOLIC AND ENDOCRINE SYSTEM FUNCTION

FIELD OF THE INVENTION

The present invention relates generally to compositions and methods for supporting the health of a subject and, more specifically, to compositions and methods for supporting the subject's metabolism and endocrine system.

BACKGROUND

Diabetes mellitus, which is referred to as "diabetes" for the sake of simplicity and has been called "the new epidemic," is believed to afflict about 18.2 million people in the United States alone, accounting for more than six percent of the U.S. population. About 13,000,000 cases of diabetes mellitus have actually been diagnosed, and new diagnoses are made at a rate of about 1.3 million every year.

Autoimmune disorders are believed to cause many cases of diabetes. Those who suffer from diabetes are unable to produce normal amounts of insulin, a substance that regulates the amount of sugar in blood. Insulin is produced by ß cells in the pancreas. In many diabetics, insulin production by the ß cells is diminished or has totally ceased. Other diabetics produce sufficient amounts of insulin to sustain normal life, but their bodies develop a "tolerance" or "resistance" to the insulin and, therefore, the insulin is unable to perform its glucose-regulating function.

There are two types of diabetes. Type I diabetes, which accounts for about five percent to about ten percent of all diabetes cases, primarily afflicts children and adolescents and, in humans, typically occurs before age 40. Thus, type I diabetes has been referred to as "early onset diabetes." In type I diabetes, a subject's pancreas produces little or no insulin. Thus, type I diabetes is typically treated with insulin to sustain the subject's life.

Type II diabetes, which has been referred to as "late onset diabetes," is responsible for about 90% to about 95% of all diabetes cases. Type II diabetes is typically caused by the inability of a subject's body to properly use insulin, which is known as "insulin resistance," or insensitivity to insulin; i.e., the cells, especially muscle cells, do not respond to insulin as effectively as they normally would. In other cases of type II diabetes, the subject's pancreas is not producing sufficient quantities of insulin or insulin production is reduced, but has not completely ceased. Insulin may be, but is not always, required to treat these types of type II diabetes. Other type II diabetics are "insulin resistant," meaning that the B cells of their pancreases produce insulin, but their bodies do not respond to the insulin as they should, or have become insensitive to the insulin. Insulin resistance is believed to be caused by oxidative stress. Many cases of type II diabetes are often treatable by lifestyle changes, including diet and exercise.

Symptoms of diabetes typically include frequent thirst ("polydipsia"), frequent hunger, frequent urination ("polyuria"), unexplained weight loss, or a combination thereof.

Diabetes may be diagnosed when the amount of glucose in the blood plasma of a subject, which is typically measured in milligrams (mg) per deciliter (dL) or millimoles (mM) per liter (L), exceeds a particular level. Typically, diabetes is diagnosed when, on at least two different days, any two of the following tests reveal that the accompanying plasma glucose level thresholds have been exceeded:

The subject suffers from symptoms of diabetes and the subject's casual (i.e., at any time of day without regard to the amount of time that has elapsed since the subject's most recent meal) plasma glucose level, or concentration, is at least 200 mg/dL, or at least 11.1 mM/L;

The subject's fasting plasma glucose (FPG) concentration, which is typically obtained first thing in the morning, before eating, is greater than or equal to 126 mg/dL, or greater than or equal to 7.0 mM/L;

The subject's two-hour post-prandial (i.e., two hours after eating) glucose (PPG) concentration, after a 75 gram glucose load, is greater than or equal to 200 mg/dL, or at least 11.1 mM/L.

A subject may be at risk of diabetes if he or she has an impaired glucose homeostasis, which is typically defined as an impaired FPG or an impaired glucose tolerance. An impaired FPG is typically defined as an FPG of 110 mg/dL to less than 126 mg/dL, or of 6.1 mM/L to less than 7.0 mM/L. An impaired glucose tolerance is typically defined as a two-hour PPG of 140 mg/dL to less than 200 mg/dL, or 7.75 mM/L to less than 11.1 mM/L.

Subjects with normal blood glucose levels typically have an FPG of less than 110 mg/dL, or 6.1 mM/L, and a two-hour PPG of less than 140 mg/dL, or 7.75 mM/L.

Physicians also use an A1C blood test, which evaluates over a long-term (e.g., 30 days) the amount of glucose in the blood. Specifically, the A1C blood test quantifies, in percent, the amount of glucose that is attached to hemoglobin molecules of red blood cells. A measurement of greater than 7.0% is high, and may indicate that a person is diabetic or at risk for diabetes. A measurement of 6.5% is normal, with lower measurements indicating less of a risk for diabetes.

A variety of secondary medical conditions may occur in diabetes patients. Diabetes is known to cause impaired vision (e.g., by cataracts and glaucoma) and even blindness. Diabetes is also believed to be responsible for about 40% of the total cases of kidney disease. In addition, diabetics often suffer nerve damage, particularly loss of sensation in extremities, including hands and feet. Diabetics may also suffer from poor cardiovascular circulation. In fact, diabetes is believed to be responsible for about 60% of non-traumatic amputations. Diabetics are also at an increased risk (by about 200% to about 400% over subjects that do not suffer from diabetes) of heart attack and stroke. Cardiovascular problems are the leading cause of death among diabetics.

Diabetes is also believed to result from an autoimmune disorder and to place diabetics at an increased risk for autoimmune disorders, in which components of a subject's immune system attack the subject's own cells or tissues. See, e.g., Biotherapy, 9(1-3): 149-57 (1996); J. Clin. Invest. 113(3):451-63 (2004); Minerva Endocrinol., 28(4):297-312 (2003); see also Diabetes Care, 27(3):813-23 (2004). Autoimmune disorders that have been associated with diabetes may be initiated through a viral infection that increases the activity of a subject's immune system. J. Immunol. 1.72(5): 3173-80 (2004).

Medical costs that are directly and indirectly associated with U.S. cases of diabetes are currently believed to be as high as about $132 billion each year. In addition to increasing healthcare costs, diabetes and the ancillary ailments that may result therefrom increase the risk of premature death. Diabetes is currently the sixth leading cause of death in the U.S., causing about 70,000 deaths in the U.S. every year, and is believed to play a role in over 200,000 deaths in the U.S. each year.

Maintaining healthy glucose (sugar) levels is an important part of pancreatic health and an even more important aspect of good health for millions of people around the world. Metabolic and endocrine disorders keep your body from producing or properly using insulin, a hormone that is needed to convert sugar, starch, and other foods into the energy needed for daily life.

There are needs for compositions and methods for supporting a subject's metabolism and endocrine system, to prevent or treat diabetes or its symptoms.

SUMMARY

The present invention includes compositions and methods for supporting a subject's metabolism and endocrine system. By way of non-limiting example, compositions and methods that incorporate teachings of the present invention facilitate support of and, thus, regulation or maintenance of, healthy levels of sugar (e.g., glucose) in blood.

In one aspect, the present invention includes compositions for supporting a subject's metabolism and endocrine system. An example of such a composition includes transfer factor, as well as one or more support components that have a positive affect on the metabolism, a component of the endocrine system, or the manner in which the endocrine system of a subject functions. As a non-limiting example, the one or more support components may be useful in directly or indirectly achieving or maintaining substantially normal levels of sugars in the blood of the subject.

Transfer factor prevents, mitigates the affects of, or reverses autoimmune disorders and oxidative stress, two causes of metabolic or endocrine system dysfunction, including, without limitation, diabetes. The one or more support components that are included in a composition according to the present invention prevent, mitigate the effects of, or reverse the causes or symptoms of metabolic or endocrine system dysfunction, such as the inability of a subject's body to properly regulate blood glucose levels.

A composition that includes transfer factor and one or more support components may support the metabolism or endocrine system function of a subject by addressing a plurality of potential symptoms of metabolic or endocrine system dysfunction.

In another aspect, the present invention includes methods for supporting a subject's metabolism and endocrine system. Such a method may, for example, include administering transfer factor and at least one support component to a subject. Administration of transfer factor and one or more support components to a diabetic subject may reduce the subject's need for insulin or medication.

Other features and advantages of the present invention will become apparent to those of skill in the art through consideration of the ensuing description and the appended claims.

DETAILED DESCRIPTION

A composition that incorporates teachings of the present invention includes transfer factor and at least one support component, which directly or indirectly supports one or both of the metabolism and endocrine system of a subject.

The transfer factor may comprise antigen-nonspecific or pathogen-nonspecific transfer factor (referred to hereinafter as "nonspecific transfer factor"), an antigen-specific or pathogen-specific transfer factor (referred to hereinafter as "specific transfer factor"), or a combination of nonspecific and specific transfer factor. Specific transfer factors are tailored for use in conditions where one or more antigens or pathogens may be present in undesirably high amounts. Although nonspecific transfer factors may have specificity for one or more antigens or pathogens, they are not tailored for use against a particular antigen or pathogen.

The transfer factor may also comprise nonmammalian transfer factor, mammalian transfer factor, or a combination of nonmammalian and mammalian transfer factors.

An example of a known nonmammalian transfer factor is the egg-derived avian transfer factor disclosed in U.S. Pat. No. 6,468,534 to Hennen et al., the disclosure of which is hereby incorporated herein, in its entirety, by this reference. Nonmammalian transfer factors that are obtained from the blood or organs of animals are also known.

Mammalian transfer factors are also known. For example, U.S. Pat. No. 4,816,563 to Wilson et al., the disclosure of which is hereby incorporated herein, in its entirety, by this reference, discloses transfer factor that has been obtained from the colostrum or milk of cows. Alternatively, or in addition, the blood or organs of mammals may serve as sources for mammalian transfer factor.

Compositions which include combinations of different types of transfer factor molecules, or transfer factor molecules from different sources, are also within the scope of the present invention. U.S. Pat. No. 6,866,868 to Lisonbee et al., the disclosure of which is hereby incorporated herein, in its entirety, by this reference, describes, among other things, compositions that include types of transfer factors, as well as transfer factors from two or more different types of source animals.

It is believed that transfer factor is useful for supporting or regulating at least two aspects of a subject's health to prevent, mitigate, or even reverse the effects of diabetes. Specifically, transfer factor may prevent, mitigate the effects of, or reverse autoimmunity and oxidative imbalance.

With respect to autoimmunity, T-regulatory cells, which include cells that were previously known as "T suppressor cells" and "T inducer cells," are at least partially responsible for recognizing various molecules, including but not limited to antigens and other proteins, as foreign (non-self) or non-foreign (self). It is believed that when autoimmune conditions are present, the T-regulatory cells do not distinguish between self and non-self. As a result, a subject's immune system may attack the subject's own cells and tissues.

In eliciting a secondary immune response, or T-cell mediated immunity, transfer factor balances the secondary immune response, rather than merely exaggerate the secondary immune response. This is evident from the examples provided in PCT International Patent Publication WO 2004/041071 A2 and A3 of Dadali et al. (hereinafter "Dadali"), the disclosure of which is hereby incorporated herein, in its entirety, by this reference. This "balancing" of a secondary immune response includes the enlistment of features or components of a secondary immune response that are not functioning properly relative to a "complete" secondary immune response. In autoimmune conditions, it is believed that "T-regulatory cells" are not distinguishing between self and non-self.

When transfer factor is administered to a subject that suffers from autoimmunity, it is believed that the immune system of the subject will respond by enlisting the T-regulatory cells. Transfer factor may also be administered to healthy individuals to facilitate maintenance of their ability to elicit a balanced secondary immune response, which includes support of the effectiveness of T-regulatory cells. Therefore, the T-regulatory cells may distinguish self from non-self and prevent, mitigate, or reverse an autoimmune response by the immune system of the subject, as well as the effects of the autoimmune response.

Transfer factor also maintains or restores oxidative balance in treated subjects, preventing or counteracting the effects of oxidative stress. This is also evident from the data provided in Dadali.

In addition to acting against two of the primary causes of diabetes, transfer factor has a beneficial effect on secondary complications that may arise from diabetes. As an example, transfer factor is useful for providing cardiovascular therapy by enlisting the immune system of a subject against pathogens, including viruses, bacteria, and other pathogenic agents, that may contribute to cardiovascular disease, which is the primary cause of death in diabetics. In enlisting the immune system of a subject, the transfer factor causes the immune system to reduce inflammation and may cause the immune system to reduce or eliminate the number of pathogens that may contribute to cardiovascular disease in the body of the subject. If specific transfer factor is used, the transfer factor may have specificity for pathogenic agents which may cause complications of metabolism- or endocrine-related disorders. For example, the composition may include transfer factor which has specificity for one or more of the herpes simplex I and II viruses (respectively, "HSV-I" and "HSV-II"), *Chlamydia pneumoniae*, cytomegalovirus ("CMV"), *Helicobacter pylori*, and various oral pathogens that may cause or exacerbate circulatory or cardiovascular disorders.

A composition that incorporates teachings of the present invention may also include one or more support components. A support component is a composition that is known or believed to support the metabolism or endocrine system of a subject. For example, a support component may support the ability of the body of a subject to metabolize nutrients or moderate nutrient levels. The support component may support or enhance one or any combination of a variety of aspects of a subject's metabolism or the activity of the subject's endocrine system.

As a more specific example, a support component of a composition according to the present invention may be useful in causing the body of a subject to moderate blood sugar (e.g., glucose) levels. For example, a support component may support maintenance of or an increase in insulin production by the B cells of the pancreas of a subject, which produce insulin, which controls (e.g., decreases) blood sugar levels. A support component may have insulin-like properties (i.e., be useful in moderating blood sugar levels). A support component may increase insulin sensitivity. A support component may decrease metabolic processes that result in glucose. A support component may prevent glucose from exiting the cells.

Alternatively, or in addition, a support component may prevent or reduce secondary complications that arise from a metabolic or endocrine system deficiency, such as diabetes. For example, a support component may improve peripheral nerve conduction and, thus, prevent or reduce symptoms of nerve damage. As another example, a support component may maintain or improve blood circulation. A support component may support maintenance of a state of cardiovascular health or improve cardiovascular health.

The foregoing examples should not be construed as limiting the scope of the invention. Some support components may support or improve more than one aspect of the metabolism or function of the endocrine system of a subject, or the general health of the subject. Of course, support components that support or improve other functions of the metabolism or endocrine system, as well as the general health of the subject, as it relates to the subject's metabolism and endocrine system function, are also within the scope of the present invention.

A composition that incorporates teachings of the present invention may include one or more support components that support the metabolism or endocrine system of a subject in one or any combination of the foregoing ways, or in other ways.

Examples of support components, to which the scope of the present invention is not to be limited, include alpha lipoic acid, bitter melon, chromium, dehydroandrosterone (DHEA), 7-oxo-DHEA, fenugreek, ginseng, gymnema, 4-hydroxyisoleucine, Indian kino, vanadium, drugs for treating diabetes, and the like. A composition that incorporates teachings of the present invention may include one of these support components, any combination of two of these support components, or any combination of three or more of these support components.

The dosages that are listed below are merely examples. Support components may be included in a composition that incorporates teachings of the present invention in lesser or greater amounts than those described hereinafter.

Alpha lipoic acid is a known antioxidant. It is also referred to as "lipoic acid," "thioctacid," "thioctan," "thioctic acid," 1, 2-dithiolane-3-valeric acid, 5-(1,2-dithiolan-3-yl) valeric acid, 6, 8-dithiooctanoic acid, and 6, 8-thioctic acid. It is believed to support and improve regulation of the levels of glucose in blood, including the effectiveness with which glucose is removed from blood, and the sensitivity of a subject's body to insulin or increase the effectiveness of insulin in the subject's body, which causes the body to reduce its production of glucose.

In addition, since alpha lipoic acid is known to be an effective antioxidant, it is useful in preventing, mitigating the effects of, or reversing the oxidative stresses that cause insulin resistance and, thus, diabetes.

The antioxidant properties of alpha lipoic acid are also useful for preventing, mitigating the effects of, or reversing kidney disease, one of the secondary complications common in diabetics that results from oxidative stress. Also due to its antioxidant abilities, alpha lipoic acid may be useful in preventing, mitigating the effects of, or treating circulatory and other cardiovascular disorders. Additional secondary benefits of alpha lipoic acid include improvement of sensory impulse conduction by peripheral nerves, which may prevent, mitigate, or reduce the effects of peripheral nerve damage that may accompany dysfunction of the metabolism or endocrine system of a subject.

Alpha lipoic acid may be included in a composition in an amount that corresponds to a daily dosage of 0 mg per kilogram (kg) of the subject's body weight to a daily dosage of about 200 mg/kg.

Bitter melon, which is also referred to as "*Momordica charantia*," "balsam apple," "balsam pear," "bitter cucumber," "bitter gourd," "carilla," "cerasee," and "karela," is believed to affect the metabolism and endocrine system function in a number of ways. For example, bitter melon may facilitate the repair of damaged B cells, which are the pancreatic cells that are responsible for making insulin. Bitter melon may stimulate the production of insulin by B cells. It may have insulin-like properties. Bitter melon decreases the synthesis of glucose by a subject.

A composition that includes bitter melon may include the bitter melon in an amount that corresponds to a daily dose of 0 mg/kg to about 4,000 mg/kg, depending upon the age of the subject and the part of the plant (e.g., fruit, seed, leaf, etc.) that is being administered. For example, a daily dose for an adult may be about 1 to 2 grams of the leaf each day, or 2.5 to 4,000 mg/kg of the fruit or an extract thereof each day.

Chromium, which may be in the form of chromium glycinate nicotinate, improves glucose levels in the blood of diabetic subjects without affecting the blood glucose levels of non-diabetic subjects. Chromium is believed to increase the number of insulin receptors, as well as the binding of insulin by the receptors. In this manner, chromium may decrease serum insulin levels and, thus, play a role in regulating the metabolism of a subject.

DHEA and 7-oxo-DHEA prevent, mitigate the effects of, or reverse insulin resistance and may improve insulin secretion by the ß cells of the pancreas. DHEA or 7-oxo-DHEA may be included in a composition according to the present invention in an amount that corresponds to a daily dose of up to about 100 mg (e.g., an amount that corresponds to a daily dose of about 50 mg).

· Fenugreek is also referred to as "*Trigonella foenum-graecum*," "bockshornsame," "fenugreco," "fenugreek," "Greek hay," and "hu lu ba." Fenugreek includes 4-hydroxyisoleucine. Fenugreek is known to lower levels of glucose and cholesterol in blood. Fenugreek also stimulates activity by pancreatic β cells, which produce insulin.

The seeds or leaves of fenugreek, or extracts thereof, may be included in a composition that incorporates teachings of the present invention. By way of example, fenugreek may be included in a composition in an amount that corresponds to a daily dosage of 0 g to about 100 g. Exemplary daily dosages are about 12.5 g to about 100 g each day, about 3 g to about 25 g each day, and about 40 mg/kg each day.

4-hydroxyisoleucine may be administered with fenugreek or separately therefrom. A composition may include 4-hydroxyisoleucine in an amount that corresponds to a daily dosage of up to about 50 mg/kg or more.

Ginseng, or *Panax schinseng*, is also referred to as "Korean ginseng," "Panax ginseng," "Asian ginseng," "ninjin," "oriental ginseng," "red ginseng," and "ren shen." Ginseng is useful in moderating blood glucose levels. It is believed that ginseng may increase insulin sensitivity (e.g., by affecting glucose receptors or enzymes that are involved in metabolic processes involving glucose) or the production and secretion of insulin by the ß cells of the pancreas.

A composition according to the present invention may include ginseng in an amount that corresponds to a daily dosage of up to six grams, depending upon the part of the plant (e.g., root, leaf, fruit, whole herb, etc.) that is administered. For example, the amount of ginseng in such a composition may correspond to a daily dosage of about 0.5 g to about 2 g.

Gymnema, or *Gymnema sylvestre*, is also referred to as "gurmar," "merasingi," "meshashringi," *Asclepias geminate, G. melicida*, and *Periploca sylvestris*. Gymnema is known to lower the levels of glucose in both type I and type II diabetics. It is believed to increase the production and secretion of insulin, as well as to decrease absorption of glucose from the digestive tract into the bloodstream.

Suitable amounts of gymnema in a composition that incorporates teachings of the present invention may correspond to a daily dosage of up to about 4 g (for leaves) or up to about 400 mg (for the GS4 extract).

Indian kino, or "*Pterocarpus masupium*," is also referred to as "Malabar kino." It is a plant bark that is believed to have insulin-like properties. Indian kino lowers glucose levels in blood and has been shown to reverse experimentally-induced diabetes.

Indian kino may be included in a composition according to the present invention in an amount that corresponds to a daily dosage of up to 6 g (e.g., about 2 g to about 4 g, about 3 g to about 6 g, etc.).

Vanadium, which is also known as "metavanadate," "orthovanadate," and "vanadyl," targets muscle cells and prevents glucose from leaving the cells. Vanadium may be used alone or synergistically with fenugreek, decreasing the amount of fenugreek that may be required to produce a desired effect and, therefore, improving safety of a composition that includes fenugreek.

Vanadium may be included in a composition according to the present invention in an amount that corresponds to a daily dosage of up to about 10 mg.

A composition of the present invention which is used to prevent, mitigate the effects of, or treat diabetes or secondary conditions resulting therefrom may include all of the foregoing elements, or it may lack some of the foregoing elements. A composition that incorporates teachings of the present invention may include additional components that are known or believed to support or improve the metabolism or endocrine system function of a treated subject.

Each support component included in a composition according to the present invention may be present in an amount that provides the desired benefits to a treated subject, but that does not disrupt the metabolism or endocrine system of the treated subject.

While the foregoing dosages and examples are described in terms of an orally administrable composition, compositions that are suitable for administration transdermally, subcutaneously, peritoneally, intravenously, or in any other manner known in the art are also within the scope of the present invention, as is administration of transfer factor and at least one support component by any known technique. Of course, the use of a non-oral administration technique may require modification of the dosage of one or more components of the administered composition.

When administered with transfer factor or with another support component, the amount of a support component that is required to provide a desired effect may be reduced due to synergism between the components, through providing a number of approaches to supporting the metabolism or endocrine system of the subject, or a combination thereof.

The following is an example of a composition that incorporates teachings of the present invention:

| EXAMPLE COMPOSITION | |
|---|---|
| Ingredient | Amount (per capsule) |
| Transfer Factor blend (30:70) | |
| Avian Transfer Factor | 15.00 mg |
| Bovine Transfer Factor | 35.00 mg |
| Fenugreek Extract | 50.00 mg |
| Pterocarbus Marsupium (Indian Kino) | 200.00 mg |
| Momordica Charantia (7% bitter principles, 0.5% Charantin) | 35.00 mg |
| Chromium Glycinate Nicotinate (2.5%) | 2.80 mg |
| Vanadium (bis-glycinato oxo vanadium) 20% | 0.75 mg |
| Korean Ginseng | 20.00 mg |
| Alpha Lipoic Acid | 30.00 mg |
| Gymnemia Sylvestre Extract (Gynemic Acid 25%) | 100.00 mg |
| TOTAL | 488.55 mg |

All percentages are by weight of the component.

All of the components of the EXAMPLE COMPOSITION are commercially available. The EXAMPLE COMPOSITION is itself available through a distributor of 4Life Research, LLC, of Sandy, Utah, as GLUCOACH™.

The transfer factor of the EXAMPLE COMPOSITION includes transfer factor from cow colostrum and avian transfer factor from chicken eggs.

As an example of the use of a composition that incorporates teachings of the present invention, one capsule of the EXAMPLE COMPOSITION may be administered orally to a subject four to six times daily. Administration of such a composition supports the metabolism and endocrine system of a subject, preventing, mitigating the effects of, or even reversing the effects of metabolic or endocrine system dysfunction.

Exemplary Benefits

A forty-eight (48) year old woman who had suffered from diabetes for more than two years had been controlling her diet and taking glucophage for several months with no perceived benefit. When initially diagnosed with diabetes, her FPG levels were about 140 mg/dL. Despite a strict diet and regular use of glucophage, her FPG levels remained at about 130 mg/dL to about 140 mg/dL. In addition to her diet and continued use of medication, she started taking two capsules of the EXAMPLE COMPOSITION twice a day (i.e., four capsules each day). During normal blood testing, she immediately noticed that her blood glucose level had dropped. This was confirmed by an A1C blood test, in which her blood glucose levels were normal. She immediately quit observing the controlled diet and quit taking glucophage. With continued use of the EXAMPLE COMPOSITION for eleven months, her blood glucose levels remain normal, with FPG measurements typically in the range of about 103 mg/dL to about 106 mg/dL. Her current A1C measure is about 6%.

A seventy-one (71) year old diabetic man had been taking glucontrol and glucophage to control his diabetes, which had persisted for more than ten years. His FPG levels were as high as 234 mg/dL, or 13 mM/L prior to taking four capsules of the EXAMPLE COMPOSITION each day (two capsules twice daily). Within a month, his FPG levels had dropped to normal and below-normal (i.e., <80 mg/dL) levels, including a ten-day stretch with measurements of 117, 83, 76, 69, 97, 116, 76, 62, 71, and 77 mg/dL. Thereafter, his FPG levels continued to be below-normal, causing his physician to reduce his dosages of glucontrol and glucophage. Thereafter, an A1G blood test indicated that glucose was attached to only about 6.9% of the hemoglobin molecules of his red blood cells, indicating that, in the long-term, his blood glucose levels had reached near-level amounts and, thus, that his body had regained some of its lost ability to produce insulin or its responsiveness to insulin.

A forty-three (43) year old woman who had suffered from type II diabetes for five years was treated with 1,000 mg of the diabetes drug metformin twice a day, 10 mg of the diabetes drug glipzide four times each day, 4 mg of the diabetes drug AVANDIA once a day, and 15 units of the synthetic human insulin HUMULIN twice each day. Immediately after taking four capsules of the EXAMPLE COMPOSITION each day (two capsules twice a day), she noticed that her blood sugar levels, which she tested throughout the day, had started dropping. Within a few days, she quit taking the diabetes drug AVANDIA and started having sugar (e.g., candy) on hand to re-increase her blood sugar levels, when needed. In addition, she rarely required the synthetic human insulin HUMULIN and she only needed to take glipzide twice a day, versus the four-times-per-day requirement before she began using the EXAMPLE COMPOSITION.

A forty-four (44) year old man who had diabetes for three years also noticed benefits soon after he began taking six capsules of the EXAMPLE COMPOSITION each day. Prior use of the EXAMPLE composition, he was required to take 1,000 mg of the diabetes drug METFORMIN twice a day, 10 mg of GLOCOTROL brand glipzide four times each day, 80 mg of the cholesterol drug LIPITOR once each day, and 50 mg of the cholesterol drug TRICOR once a day to keep his diabetes under control. In the year before taking the EXAMPLE COMPOSITION, his FPG levels had consistently been between 300 mg/dl and 400 mg/dL despite taking his medication as instructed by his physician. Within a day of initiating a four capsule per day (two capsules twice a day) regimen of the EXAMPLE composition, his FPG levels were consistently less than 200 mg/dl.

These results indicate that a composition that incorporates teachings of the present invention addresses needs that may not be addressed by insulin or prescription medications, and that treatment with such a composition may reduce a diabetic's reliance upon insulin or prescription medications.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A composition in an oral dosage form, the composition consisting of effective amounts of:
    50 mg of a transfer factor-containing component consisting of a source blend of bovine colostrum and chicken egg yolk, the transfer factor-containing component including a non-specific transfer factor;
    405 mg of a botanical support component consisting of *Pterocarpus marsupium*, *Gymnema sylvestre*, fenugreek, *Momordica charantia*, and ginseng;
    2.8 mg of chromium glycinate nicotinate;
    0.75 mg of vanadium; and
    30 mg of alpha-lipoic acid.

2. A composition capable of mitigating or reversing effects of autoimmune disorders in a body of a subject, the composition being in an oral dosage form and consisting of effective amounts of:
    50 mg of a transfer factor-containing component;
    405 mg of a botanical support component consisting of *Pterocarpus marsupium*, *Gymnema sylvestre*, fenugreek, *Momordica charantia*, and ginseng;
    2.8 mg of chromium glycinate nicotinate;
    0.75 mg of vanadium; and
    30 mg of alpha-lipoic acid.

3. The composition of claim 2, wherein the transfer factor consists of at least one of a mammalian transfer factor source and a nonmammalian transfer factor source.

4. A composition in an oral dosage form and consisting of effective amounts of:
    a transfer factor-containing component from at least one of colostrum and egg, the transfer factor-containing component comprising a combination of a non-specific transfer factor and a specific transfer factor;
a botanical support component consisting of *Pterocarpus marsupium*, *Gymnema sylvestre*, fenugreek, *Momordica charantia*, and ginseng; and
an antioxidant consisting of alpha lipoic acid.

5. The composition of claim 4, wherein the transfer factor-containing component comprises at least one of mammalian transfer factor and nonmammalian transfer factor.

6. The composition of claim 4, wherein the oral dosage form of the composition includes:
   50 mg of the transfer factor-containing component; and
   405 mg of a combination of the fenugreek, the *Pterocarpus marsupium*, the *Momordica charantia*, the ginseng, and the *Gymnema sylvestre*.

7. The composition of claim 4, wherein the oral dosage form of the composition includes:
   30 mg of the alpha lipoic acid.

8. A dose of a composition consisting of effective amounts of:
   transfer factor sources;
   fenugreek;
   *Pterocarpus marsupium*;
   *Momordica charantia*;
   chromium;
   vanadium;
   ginseng;
   alpha lipoic acid; and
   *Gymnema sylvestre*,
   the dose of the composition decreasing oxidative stress and mitigating effects of autoimmune disorders in a subject.

9. The composition of claim 8, wherein the transfer factor sources are egg yolk and colostrum.

10. The composition of claim 9, wherein the colostrum is bovine colostrum.

11. The composition of claim 9, wherein the egg yolk is chicken egg yolk.

12. The composition of claim 8, wherein the *Momordica charantia* is obtained from a fruit of *Momordica charantia*.

13. The composition of claim 8, wherein the oral dosage form of the composition includes:
   50 mg of the transfer factor-containing component;
   405 mg of a combination of the fenugreek, the *Pterocarpus marsupium*, the *Momordica charantia*, the ginseng, and the *Gymnema sylvestre*;
   30 mg of the alpha lipoic acid; and
   0.75 mg of the vanadium.

* * * * *